US011950957B2

(12) United States Patent
Ryu et al.

(10) Patent No.: US 11,950,957 B2
(45) Date of Patent: Apr. 9, 2024

(54) DISPLAY DEVICE AND SYSTEM FOR ULTRASOUND IMAGE, AND METHOD FOR DETECTING SIZE OF BIOLOGICAL TISSUE BY USING SAME

(71) Applicant: HEALCERION CO., LTD., Seoul (KR)

(72) Inventors: Jeong Won Ryu, Seoul (KR); You Chan Choung, Seoul (KR)

(73) Assignee: HEALCERION CO., LTD., Gyeonggi-do (KR)

( * ) Notice: Subject to any disclaimer, the term of this patent is extended or adjusted under 35 U.S.C. 154(b) by 466 days.

(21) Appl. No.: 17/252,817

(22) PCT Filed: Jun. 19, 2019

(86) PCT No.: PCT/KR2019/007363
§ 371 (c)(1),
(2) Date: Dec. 16, 2020

(87) PCT Pub. No.: WO2020/004855
PCT Pub. Date: Jan. 2, 2020

(65) Prior Publication Data
US 2021/0145408 A1 May 20, 2021

(30) Foreign Application Priority Data
Jun. 28, 2018 (KR) .................. 10-2018-0074590

(51) Int. Cl.
*A61B 8/00* (2006.01)
*A61B 8/08* (2006.01)
(Continued)

(52) U.S. Cl.
CPC ................ *A61B 8/467* (2013.01); *A61B 8/14* (2013.01); *A61B 8/463* (2013.01); *A61B 8/465* (2013.01);
(Continued)

(58) Field of Classification Search
CPC .......... A61B 8/467; A61B 8/14; A61B 8/463; A61B 8/465; A61B 8/5207; A61B 8/54;
(Continued)

(56) References Cited

U.S. PATENT DOCUMENTS 9,314,225 B2 * 4/2016 Steen .................. A61B 8/5207
11,259,874 B1 * 3/2022 Landon ................. G16H 40/67
(Continued)

FOREIGN PATENT DOCUMENTS

CN 103455710 A 12/2013
JP 2008-253379 A 10/2008
(Continued)

OTHER PUBLICATIONS

Office Action from corresponding Chinese Patent Application No. 201980043851.5, dated Jul. 29, 2023.
(Continued)

*Primary Examiner* — Sanjay Cattungal
(74) *Attorney, Agent, or Firm* — Harness, Dickey & Pierce, P.L.C.

(57) ABSTRACT

A display device for an ultrasound image, according to one embodiment of the present invention, comprises: an input/output interface unit including a touch screen for displaying an ultrasound image of a biological tissue so as to recognize a user's touch point when the user touches the touch screen on which the ultrasound image is displayed; an edge detection unit for detecting at least one edge portion that is adjacent to the recognized touch point on the ultrasound image; and a control unit for controlling an edge curve, corresponding to the detected edge portion, to be superposed and displayed onto the ultrasound image, and detecting size information about the biological tissue according to the type
(Continued)

of the displayed edge curve, wherein the input/output interface outputs, according to the control of the control unit, the detected size information.

12 Claims, 7 Drawing Sheets

(51) Int. Cl.
| | | |
|---|---|---|
| *A61B 8/14* | (2006.01) | |
| *G06F 3/0488* | (2022.01) | |
| *G06T 7/13* | (2017.01) | |
| *G06T 7/136* | (2017.01) | |
| *G06T 7/62* | (2017.01) | |
| *G16H 30/40* | (2018.01) | |
| *G16H 40/63* | (2018.01) | |
| *G16H 50/20* | (2018.01) | |

(52) U.S. Cl.
CPC .............. *A61B 8/5207* (2013.01); *A61B 8/54* (2013.01); *A61B 8/56* (2013.01); *G06F 3/0488* (2013.01); *G06T 7/13* (2017.01); *G06T 7/136* (2017.01); *G06T 7/62* (2017.01); *G16H 30/40* (2018.01); *G16H 40/63* (2018.01); *G16H 50/20* (2018.01); *G06T 2200/24* (2013.01); *G06T 2207/10132* (2013.01); *G06T 2207/20104* (2013.01)

(58) Field of Classification Search
CPC ......... A61B 8/56; A61B 8/461; A61B 8/0866; A61B 8/0891; A61B 8/468; A61B 8/469; A61B 8/5223; G06F 3/0488; G06T 7/13; G06T 7/136; G06T 7/62; G06T 2200/24; G06T 2207/10132; G06T 2207/20104; G16H 30/40; G16H 40/63; G16H 50/20
See application file for complete search history.

(56) References Cited

U.S. PATENT DOCUMENTS

| | | | | |
|---|---|---|---|---|
| 2003/0139664 | A1* | 7/2003 | Hunt .................... | G01S 7/52023 600/407 |
| 2004/0158154 | A1* | 8/2004 | Hanafy ............... | G01S 7/52053 600/446 |
| 2008/0249414 | A1* | 10/2008 | Yang .................... | A61B 8/0883 600/445 |
| 2009/0275835 | A1* | 11/2009 | Hwang ................ | A61B 8/4433 600/443 |
| 2011/0050594 | A1* | 3/2011 | Kim .................... | G06F 3/04847 345/173 |
| 2012/0133601 | A1* | 5/2012 | Marshall ................ | G16H 30/20 345/173 |
| 2013/0019193 | A1* | 1/2013 | Rhee .................... | G06F 3/04886 715/764 |
| 2013/0218024 | A1* | 8/2013 | Boctor ................. | A61B 5/0077 600/476 |
| 2013/0226001 | A1* | 8/2013 | Steen ................... | G01S 7/52096 600/447 |
| 2013/0328810 | A1* | 12/2013 | Li ....................... | G06F 3/04883 345/173 |
| 2014/0009686 | A1* | 1/2014 | Segal .................... | H04N 5/2222 348/722 |
| 2014/0100440 | A1* | 4/2014 | Cheline ................ | A61B 5/0066 600/407 |
| 2014/0111451 | A1* | 4/2014 | Park ..................... | G06F 3/04883 345/173 |
| 2014/0164965 | A1* | 6/2014 | Lee ........................ | A61B 8/467 715/765 |
| 2014/0180111 | A1* | 6/2014 | Gopinathan ........... | A61B 8/483 600/447 |
| 2014/0200452 | A1* | 7/2014 | Chang ...................... | G06T 7/12 600/407 |
| 2014/0200456 | A1* | 7/2014 | Owen .................. | A61B 8/4427 600/447 |
| 2016/0085328 | A1 | 3/2016 | Lee et al. | |
| 2017/0028227 | A1* | 2/2017 | Emery ...................... | A61N 7/02 |
| 2018/0085043 | A1* | 3/2018 | Panicker ................ | A61B 5/204 |
| 2018/0365808 | A1* | 12/2018 | Jiang ....................... | G06T 5/002 |
| 2019/0156526 | A1* | 5/2019 | Liu ............................. | G06T 7/90 |
| 2020/0004225 | A1* | 1/2020 | Buller .................... | B29C 64/393 |
| 2021/0015456 | A1* | 1/2021 | Chiang ................ | A61B 8/0883 |

FOREIGN PATENT DOCUMENTS

| | | |
|---|---|---|
| JP | 2014-097127 A | 5/2014 |
| KR | 10-2007-0039232 A | 4/2007 |
| KR | 10-2011-0062727 A | 6/2011 |
| KR | 10-2011-0136108 A | 12/2011 |
| KR | 10-2014-0112343 A | 9/2014 |
| KR | 10-1599891 B1 | 3/2016 |

OTHER PUBLICATIONS

Office Action from corresponding Korean Patent Application No. 10-2018-0074590, dated Jan. 22, 2020.
International Search Report from corresponding PCT Application No. PCT/KR2019/007363, dated Sep. 25, 2019.

* cited by examiner

DISPLAY DEVICE AND SYSTEM FOR ULTRASOUND IMAGE, AND METHOD FOR DETECTING SIZE OF BIOLOGICAL TISSUE BY USING SAME

CROSS-REFERENCE TO RELATED APPLICATIONS

This application is a national phase application of PCT International Application No. PCT/KR2019/007363, filed on Jun. 19, 2019, which claims priority to Korean Patent Application Nos. 10-2018-0074590, filed on Jun. 28, 2018. The entire disclosure of the applications identified in this paragraph is incorporated herein by references.

FIELD

The present invention relates to an ultrasound image technique for displaying an image inside a body of a human or an animal, that is, a medical image of biological tissue, and more particularly, to a technique for detecting a size of biological tissue included in a captured ultrasound image.

BACKGROUND

Medical imaging apparatuses are configured to obtain a biological image of a human, an animal, or the like. Medical imaging apparatuses are noninvasive inspection apparatuses configured to capture and process images of details in a body, internal organs, fluid flow, and the like to show them to a user. Users such as roentgenologists and the like may diagnose a health condition and a disease of a patient using an output medical image. As a representative one of medical imaging apparatuses, there are an ultrasound imaging apparatus, an X-ray apparatus, a computerized tomography (CT) apparatus, a magnetic resonance imaging (MRI) apparatus, and the like.

Particularly, an ultrasound imaging apparatus is an apparatus configured to emit ultrasonic waves of several MHz or higher toward an inside of a body and detect waves reflected or scattered from tissue inside the body so as to display the tissue inside the body using a reflection time and reflection intensity. Since such ultrasound imaging apparatuses show biological tissue such as internal organs, bones, disks, articulations, nerves, ligaments, and the like from a desired viewpoint, ultrasound imaging apparatuses are generally used for accurately diagnosing a disease.

In order to detect a size of biological tissue using one of ultrasound imaging apparatuses, it is necessary to move a mouse (or a cursor) to biological tissue to be detected from a captured ultrasound image of biological tissues and to perform point designation two or more times for measuring a distance of the corresponding biological tissue.

However, in a point designation process, it is not easy to designate a point for measuring the distance of the corresponding biological tissue at a precise spot. Even when the point is designated, since it is necessary to continuously perform two or more point designation processes, a process for detecting the size of the biological tissue is complicated.

SUMMARY

Technical Problem

The present invention is directed to providing an ultrasound image display device and system configured to measure a precise size of biological tissue included in an ultrasound image with only a simple manipulation and a biological tissue size detection method using the same.

Technical Solution

One aspect of the present invention provides an ultrasound image display device including an input/output interface portion including a touch screen, which displays an ultrasound image of biological tissue, and configured to recognize a touch point of a user who touches the touch screen on which the ultrasound image is displayed, an edge detection portion configured to detect at least one edge part adjacent to the recognized touch point in the ultrasound image, and a control portion configured to control an edge curve corresponding to the detected edge part to be displayed while being overlapped with the ultrasound image and to detect size information of the biological tissue according to a type of the displayed edge curve. Here, the input/output interface portion outputs the detected size information under the control of the control portion.

The edge detection portion may detect, as the edge part, points having a brightness variation higher than or equal to a threshold on the basis of the touch point from a grayscale image of the ultrasound image.

The control portion may determine whether the type of the edge curve is an open curve or a closed curve. Here, when the type of the edge curve is the open curve, the control portion may detect, as the size information, a distance between virtual touch points at which extended virtual normal lines perpendicular to two open edge curves formed on both sides of the touch point meet the open edge curves.

When the type of the edge curve is the closed curve, the control portion may detect two virtual points corresponding to a longest distance on the closed edge curve formed around the touch point and may detect size information corresponding to a perimetric length of the closed edge curve using a first distance of a virtual line connecting the detected virtual points and a second distance between two virtual touch points corresponding to a longest distance among virtual touch points at which a virtual normal line perpendicular to the virtual line meets the closed edge curve.

The ultrasound image display device may further include a display communication portion configured to receive ultrasound image data from an ultrasound image diagnosis apparatus configured to generate the ultrasound image data corresponding to the biological tissue using an ultrasound probe. Here, when the ultrasound image data is received through the display communication portion, the input/output interface portion may display an ultrasound image corresponding to the received ultrasound image data on the touch screen.

Another aspect of the present invention provides an ultrasound image display system including an ultrasound image diagnosis apparatus configured to generate ultrasound image data corresponding to biological tissue using an ultrasound probe and to transmit the generated ultrasound image data and a display device configured to receive the ultrasound image data from the ultrasound image diagnosis apparatus and to display an ultrasound image corresponding to the ultrasound image data on a screen using the received ultrasound image data. Here, the display device includes an input/output interface portion including a touch screen, which displays the ultrasound image, and configured to recognize a touch point of a user who touches the touch screen on which the ultrasound image is displayed, an edge detection portion configured to detect at least one edge part adjacent to the recognized touch point in the ultrasound image, and a control portion configured to control an edge curve corresponding to the detected edge part to be displayed while being overlapped with the ultrasound image and to detect size information of the biological tissue according to a type of the displayed edge curve. Also, the input/output interface portion outputs the detected size information under the control of the control portion.

The ultrasound image diagnosis apparatus may include the ultrasound probe configured to transmit an ultrasonic signal to the biological tissue and then to receive an ultrasonic echo signal reflected from the biological tissue, an ultrasound image generation portion configured to generate ultrasound image data corresponding to the ultrasonic echo signal received by the ultrasound probe, a diagnosis communication portion configured to transmit the generated ultrasound image data to the display device, and a power supply portion including a battery charged with power and exhausting the power and configured to supply power for driving the ultrasound image generation portion and the communication portion using the power charged in the battery.

The ultrasound image generation portion may include a pulse generation module configured to generate a high-voltage electrical pulse for generating the ultrasonic signal, a signal processing module configured to amplify and convert the ultrasonic echo signal into a digital signal, a transmission/reception module configured to transmit the high-voltage pulse generated by the pulse generation module to the ultrasound probe or to receive and forward the ultrasonic echo signal from the ultrasound probe to the signal processing module, a beamforming module configured to allow the pulse generation module to generate the high-voltage pulse corresponding to the ultrasound probe, to receive the digital signal from the signal processing module, and to generate the ultrasound image data corresponding to the ultrasound probe, and a processing module configured to control the beamforming module to perform beamforming corresponding to the ultrasound probe and to control the ultrasound image data received from the beamforming module to be transmitted to the display device.

Still another aspect of the present invention provides a method of detecting a size of biological tissue using an ultrasound image display device. The method includes displaying an ultrasound image of biological tissue on a touch screen, recognizing a touch point of a user who touches the touch screen on which the ultrasound image is displayed, detecting at least one edge part adjacent to the recognized touch point from the ultrasound image, displaying an edge curve corresponding to the detected edge part to be overlapped with the ultrasound image, detecting size information of the biological tissue according to a type of the displayed edge curve, and outputting the detected size information.

The detecting of the edge part may include detecting, as the edge part, points having a brightness variation higher than or equal to a threshold on the basis of the touch point from a grayscale image of the ultrasound image.

The detecting of the size information of the biological tissue may include determining whether the type of the edge curve is an open curve or a closed curve and detecting, when the type of the edge curve is the open curve, as the size information, a distance between virtual touch points at which extended virtual normal lines perpendicular to two open edge curves formed on both sides of the touch point meet the open edge curves.

The detecting of the size information of the biological tissue may include, when the type of the edge curve is the closed curve, detecting two virtual points corresponding to a longest distance on the closed edge curve formed around the touch point and detecting size information corresponding to a perimetric length of the closed edge curve using a first distance of a virtual line connecting the detected virtual points and a second distance between two virtual touch points corresponding to a longest distance among virtual touch points at which a virtual normal line perpendicular to the virtual line meets the closed edge curve.

The method may further include receiving ultrasound image data from an ultrasound image diagnosis apparatus configured to generate the ultrasound image data corresponding to the biological tissue using an ultrasound probe. Here, the ultrasound image is displayed on the touch screen after the receiving of the ultrasound image data.

Advantageous Effects

According to the present invention, a touch point of a user who touches a touch screen on which an ultrasound image is displayed is recognized and size information of biological tissue is detected according to the type of an edge curve corresponding to an edge part adjacent to the recognized touch point so that there is provided convenience of obtaining accurate size information of the biological tissue through only one touch manipulation of the user.

DETAILED DESCRIPTION

Figure 1:
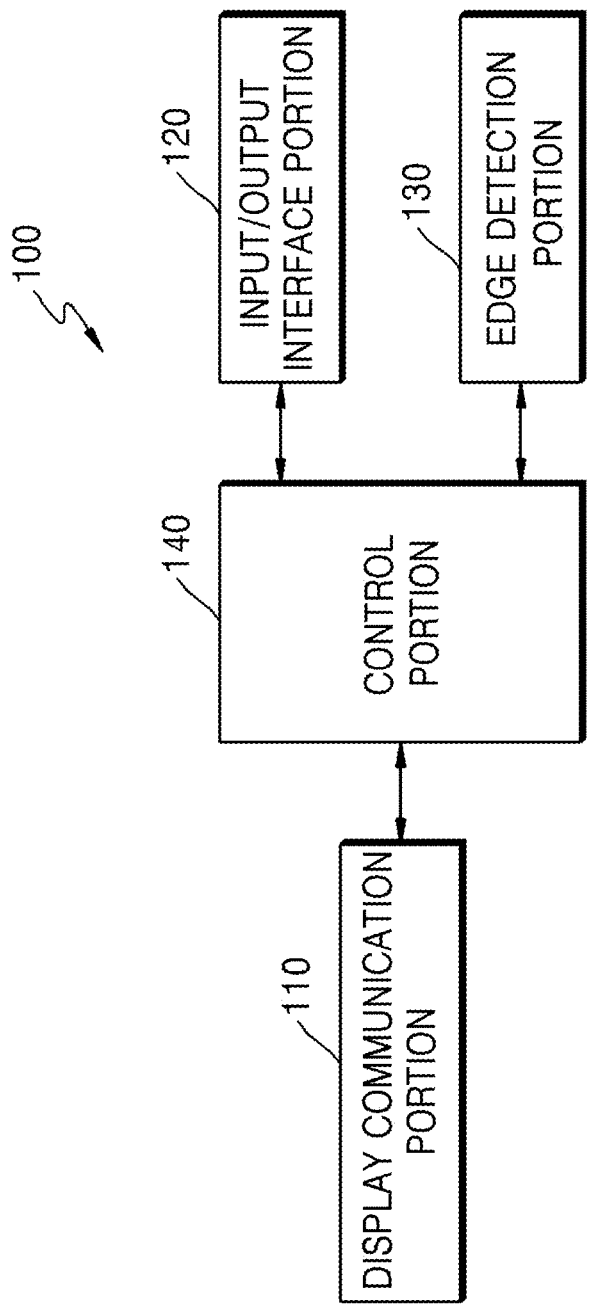
FIG. 1 is a block diagram illustrating components of an ultrasound image display device according to one embodiment of the present invention.

Hereinafter, exemplary embodiments of the present invention will be described in detail with reference to the attached drawings.

Embodiments of the present invention are provided to more completely explain the present invention to one of ordinary skill in the art. The embodiments of the present invention may be modified to have a variety of shapes, and the scope of the present invention is not limited to the following embodiments. The embodiments are provided to make the present disclosure more substantial and complete and to completely transfer the concept of the present invention to those skilled in the art.

The terms are used herein to explain particular embodiments and not intended to limit the present invention. As used herein, singular expressions, unless clearly defined otherwise in context, include plural expressions. Also, the terms such as "comprise" and/or "comprising" are not specify stated a shape, a number, an operation, a member, an element, and/or a group thereof and do not exclude presence or addition of one or more other shapes, numbers, operations, members, elements, and/or groups. Also, as used herein, the term "and/or" includes any and all combinations or one of a plurality of associated listed items.

In the specification, although the terms such as first, second, and the like are used for describing a variety of members, regions, and/or parts, it is apparent that the members, components, regions, layers, and/or parts should not be limited to the above terms. The terms do not mean a particular sequence, upper and lower classes, or dominance and are used only for distinguishing one member, region or part from another member, region, or part. Accordingly, a first member, region, or part which will be described below may be referred to as a second member, region, or part without departing from the teachings of the present invention.

Also, hereinafter, the embodiments of the present invention will be described with reference drawings which schematically illustrate the embodiments of the present invention. Throughout the drawings, for example, according to manufacturing technique and/or tolerances, modifications of shapes shown in the drawings may be perceived. Accordingly, the embodiments of the present invention should not be construed as being limited to particular shapes of regions shown in the drawings and should include, for example, changes in shapes caused in manufacturing.

FIG. 1 is a block diagram illustrating components of an ultrasound image display device 100 according to one embodiment of the present invention.

Referring to FIG. 1, the display device 100 may include a display communication portion 110, an input/output interface portion 120, an edge detection portion 130, and a control portion 140.

The display communication portion 110 may set communication between the display device 100 and an external device (for example, an ultrasound image diagnosis apparatus or the like which will be described below). The display communication portion 110 may communicate with an external device through wireless communication or wired communication and include a communication module for wireless communication or wired communication.

Here, wireless communication may include, as a cellular communications protocol, long-term evolution (LTE), LTE-Advanced (LTE-A), code-division multiple access (CDMA), wideband CDMA (WCDMA), universal mobile telecommunication system (UMTS), wireless broadband (WiBro), a global system for mobile communications (GSM), or the like and may also include, as short-range wireless communication, Bluetooth, WiFi, ZigBee, and the like. Also, wired communication may include, for example, universal serial bus (USB), high-definition multimedia interface (HDMI), recommended standard 232 (RS-232), plain old telephone service (POTS), or the like.

The display communication portion 110 receives ultrasound image data from the ultrasound image diagnosis apparatus configured to generate ultrasound image data corresponding to biological tissue using an ultrasound probe. The display communication portion 110 may receive ultrasound image data through wireless communication or wired communication. The received ultrasound image data may be stored in a memory included in the control portion 140 which will be described below or a separate memory space (not shown).

The input/output interface portion 120 transmits an instruction or data input from a user to other components of the display device 100. Also, the input/output interface portion 120 outputs instructions or data received from other components of the display device 100 as image signals or voice signals. In order to receive an instruction or data from the user, the input/output interface portion 120 may include an input device such as a touch screen, a keyboard, a scanning pen, and the like. The touch screen may use, for example, at least one of an electrostatic method, a resistive method, an infrared method, and an ultrasonic method. Also, the input/output interface portion 120 outputs instructions or data received from other components of the electronic device as images or voices. To output an image, the input/output interface portion 120 may include a liquid crystal display (LCD), a light emitting diode (LED) display, an organic LED (OLED) display, and the like.

The input/output interface portion 120 displays an ultrasound image corresponding to ultrasound image data received through the display communication portion 110 or stored in the memory space. Particularly, the input/output interface portion 120 recognizes a touch point of the user who touches the touch screen on which the ultrasound image is displayed. The input/output interface portion 120 may recognize the touch point of the user by checking a coordinate value of the touch point on the touch screen where the user touches.

Figure 2A:
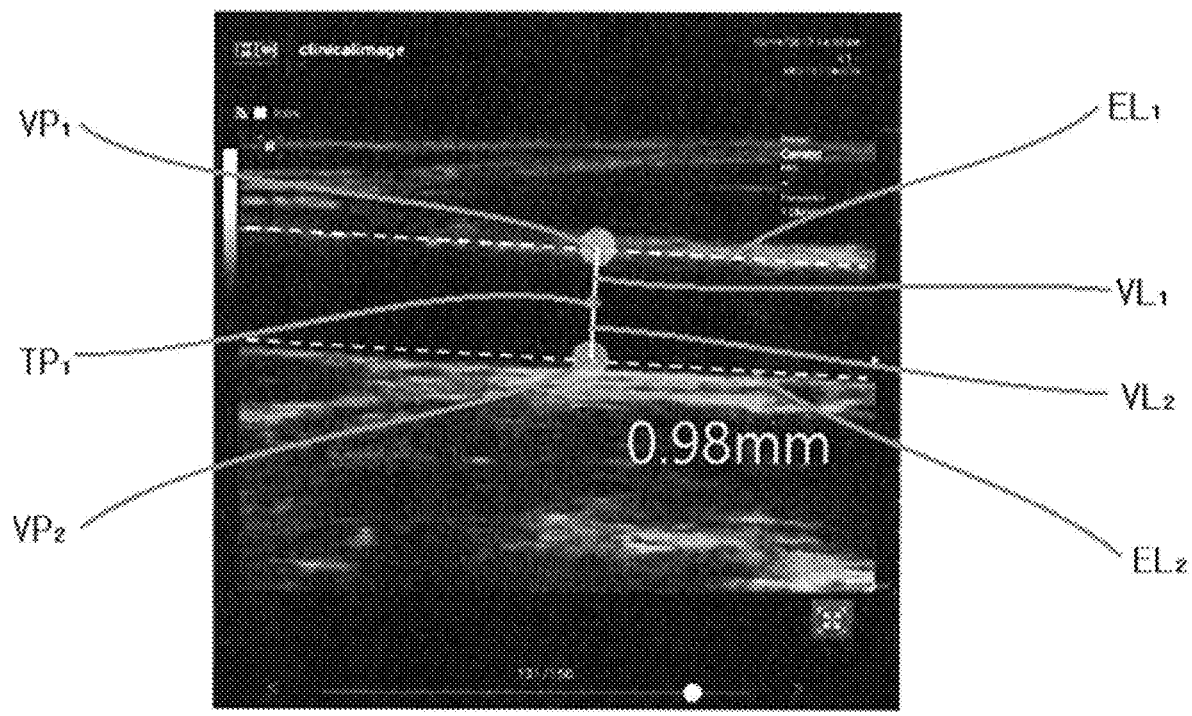
FIGS. 2A and 2B are reference views illustrating ultrasound images displayed on an input/output interface portion shown in FIG. 1.
Figure 2B:
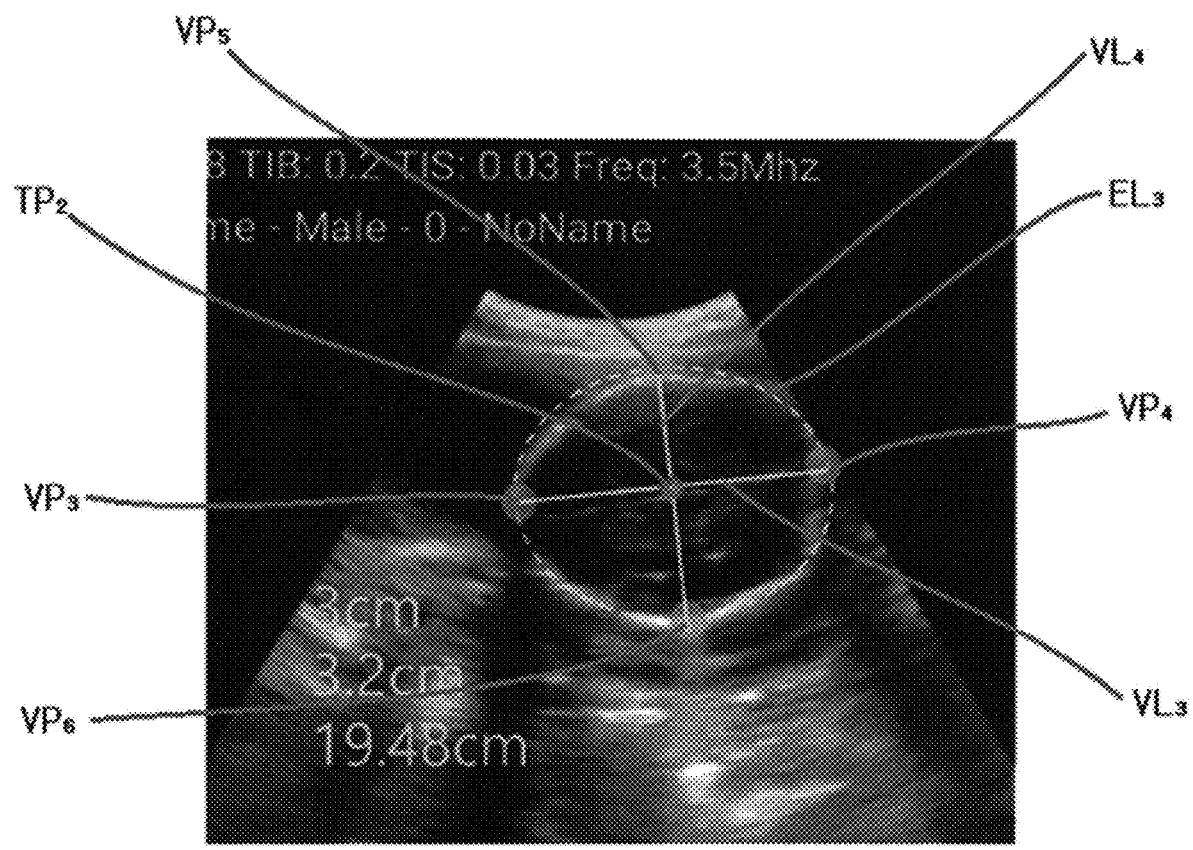

FIGS. 2A and 2B are reference views illustrating ultrasound images displayed on the input/output interface portion shown in FIG. 1. FIG. 2A illustrates an ultrasound image of a blood vessel among biological tissue, and FIG. 2B illustrates an ultrasound image of a fetal head among biological tissues.

Referring to FIG. 2A, when the user (for example, a roentgenologist) touches a central part of the blood vessel with a finger (for example, a long touch), the input/output interface portion 120 recognizes a corresponding touch point as a touch point TP. Also, referring to FIG. 2B, when the user touches a central part of the fetal head with a finger, the input/output interface portion 120 recognizes a corresponding touch point as a touch point TP of the user.

The edge detection portion 130 detects one or more edge parts adjacent to a recognized touch point in an ultrasound image. The edge detection portion 130 may detect an edge part most adjacent to the touch point using an image processing algorithm for detecting an edge. For example, the edge detection portion 130 may detect, as edge parts, points which have a brightness variation higher than or equal to a threshold on the basis of the touch point from a grayscale image of the ultrasound image.

The ultrasound image may correspond to the grayscale image. Accordingly, the edge detection portion 130 detects an edge part directly adjacent to the touch point recognized at the input/output interface portion 120 from the grayscale image of the ultrasound image. To detect the edge part, the edge detection portion 130 determines whether a brightness value of the adjacent point is higher than or equal to a certain threshold in comparison to a brightness value of the touch point. When the brightness value of the adjacent point is lower than the certain threshold in comparison to the brightness value of the touch point, the edge detection portion 130 determines that a corresponding image region is not the edge part. Also, when the brightness value of the adjacent point is higher than or equal to the certain threshold in comparison to the brightness of the touch point, the edge detection portion 130 determines that the corresponding image region is the edge part.

Referring to FIG. 2A, the edge detection portion 130 may detect a blood vessel wall image, that is, two white line image regions located above and below a touch point $TP_1$ as edge parts directly adjacent to the touch point $TP_1$. Also, referring to FIG. 2B, the edge detection portion 130 may detect a fetal head image, that is, an white elliptical image region located around a touch point $TP_2$ as an edge part directly adjacent to the touch point $TP_2$.

The control portion 140 may include one or more of a central processing unit (CPU), an application processor (AP), and a communication processor (CP) and also include a memory. The control portion 140 may perform calculation or data processing with respect to control and/or communication of components included in the display device 100. Also, the memory included in the control portion may include a volatile and/or a nonvolatile memory.

The memory may store instruction or program information of the display device 100 to detect size information and may store ultrasound image data received through the input/output interface portion 120.

The control portion 140 controls an edge curve corresponding to the detected edge part to be displayed while being overlapped with the ultrasound image and detects size information of the biological tissue according to a type of the displayed edge curve.

Referring to FIG. 2A, the control portion 140 controls the edge curve corresponding to the edge part to be displayed while being overlapped with the ultrasound image so that the input/output interface portion 120 displays edge curves $EL_1$ and $EL_2$ on the ultrasound image to be overlapped with the edge parts (for example, the blood vessel wall image) adjacent to the touch point $TP_1$. Here, the input/output interface portion 120 may display the edge curves $EL_1$ and $EL_2$ as solid lines, dotted lines, or the like and may display the edge curves $EL_1$ and $EL_2$ in color different from the edge part.

Also, referring to FIG. 2B, the control portion 140 controls the edge curve corresponding to the edge part to be displayed while being overlapped with the ultrasound image so that the input/output interface portion 120 displays an edge curve $EL_3$ to be overlapped with the edge part (for example, the fetal head image) adjacent to the touch point $TP_2$. In this case, the input/output interface portion 120 may display the edge curve $EL_3$ as a solid line, a dotted line, or the like and may display the edge curve $EL_3$ in color different from the edge part.

The control portion 140 determines whether the type of the edge curve is an open curve or a closed curve and detects size information corresponding to the determined type of curve. Here, the open curve corresponds to a line in which ends of an edge curve are not connected. For example, as shown in FIG. 2A, a segment corresponding to the blood vessel wall may correspond to the open curve. Also, the closed curve is a line in which both ends of an edge curve are connected to each other. For example, as shown in FIG. 2B, an elliptical curve corresponding to the fetal head may correspond to the closed curve.

The control portion 140 may detect whether both ends of the edge curve are connected to each other and determine a curve type of the corresponding edge curve. However, even when both ends of the edge curve are not connected completely, the control portion 140 may determine the edge curve to be a closed curve when the curve has a closed curve shape.

When the type of the edge curve is an open curve, the control portion 140 may virtually extend normal lines perpendicular to two edge curves formed on both sides of the touch point and may detect a distance between virtual touch points which meet the open edge curves as the size information.

Referring to FIG. 2A, the control portion 140 determines a type of the two edge curves $EL_1$ and $EL_2$ (hereinafter, referred to as the open edge curves) formed on both sides on the basis of the touch point $TP_1$. In the case of the open edge curve, virtual normal lines $VL_1$ and $VL_2$ starting from the touch point $TP_1$ to be perpendicular to the open edge curves $EL_1$ and $EL_2$ are extended and points at which the extended virtual normal lines $VL_1$ and $VL_2$ meet the open edge curves $EL_1$ and $EL_2$, that is, virtual touch points $VP_1$ and $VP_2$ are detected. Subsequently, the control portion 140 detects a distance between the detected virtual touch points $VP_1$ and $VP_2$ as size information with respect to the biological tissue (for example, a blood vessel) using position information (for example, coordinate information) of the detected virtual touch points $VP_1$ and $VP_2$.

Also, when the type of the edge curve is the closed curve, the control portion 140 may detect two virtual points corresponding to a longest distance on the edge curve formed around the touch point and may detect, as size information, a first distance of a virtual line connecting the detected virtual points and a second distance between two virtual touch points corresponding to a longest distance among virtual touch points at which a virtual normal line perpendicular to the virtual line meets the edge curve. Also, the control portion 140 may detect size information corresponding to a perimetric length of a closed edge curve using information on the first distance and the second distance.

Referring to FIG. 2B, the control portion 140 determines a type of the edge curve $EL_3$ (hereinafter, referred to as the closed edge curve) formed around the touch point $TP_2$. Subsequently, when the type is the closed edge curve $EL_3$, virtual points on the closed edge curve $EL_3$ are determined and then two virtual points $VP_3$ and $VP_4$ corresponding to a longest distance are detected from the determined virtual points. Accordingly, the control portion 140 detects a first distance of a virtual line $VL_3$ connecting the virtual points $VP_3$ and $VP_4$ as a longer distance of the closed curve corresponding to the biological tissue (for example, the fetal head) using position information (for example, coordinate information) of the detected virtual points $VP_3$ and $VP_4$. Also, the control portion 140 sets a virtual normal line perpendicular to the virtual line $VL_3$ connecting the virtual points $VP_3$ and $VP_4$ and detects two virtual touch points $VP_5$ and $VP_6$ corresponding to a longest distance from virtual points at which the set virtual normal line meets the closed edge curve $EL_3$. Accordingly, the control portion 140 detects a second distance of a virtual normal line $VL_4$ virtually connecting the virtual points $VP_5$ and $VP_6$ as a shorter distance of the closed curve corresponding to the biological tissue (for example, the fetal head) using position information (for example, coordinate information) of the detected virtual points $VP_5$ and $VP_6$. Subsequently, the control portion 140 may detect an approximate perimeter length, that is, size information of the closed edge curve using a formula for obtaining a perimeter of an elliptical closed curve, a circular closed curve, or the like on the basis of the detected first distance and second distance.

Meanwhile, the virtual touch points or virtual points $VP_1$, $VP_2$, $VP_3$, $VP_4$, $VP_5$, and $VP_6$ displayed on the touch screen of the input/output interface portion 120 may vary on the open edge curves $EL_1$ and $EL_2$ or the closed edge curve $EL_3$ depending on a manipulation of the user. When the virtual touch points or virtual points $VP_1$, $VP_2$, $VP_3$, $VP_4$, $VP_5$, and $VP_6$ vary according to the manipulation of the user, the control portion 140 may detect size information of the biological tissue using position information (for example, coordinate information) among the virtual touch points or virtual points $VP_1$, $VP_2$, $VP_3$, $VP_4$, $VP_5$, and $VP_6$ which have varied.

Subsequently, the control portion 140 controls the input/output interface portion 120 to output the detected size information of the biological tissue so that the input/output interface portion 120 may display the size information of the biological tissue on the ultrasound image or output the size information as voice information.

Figure 3:
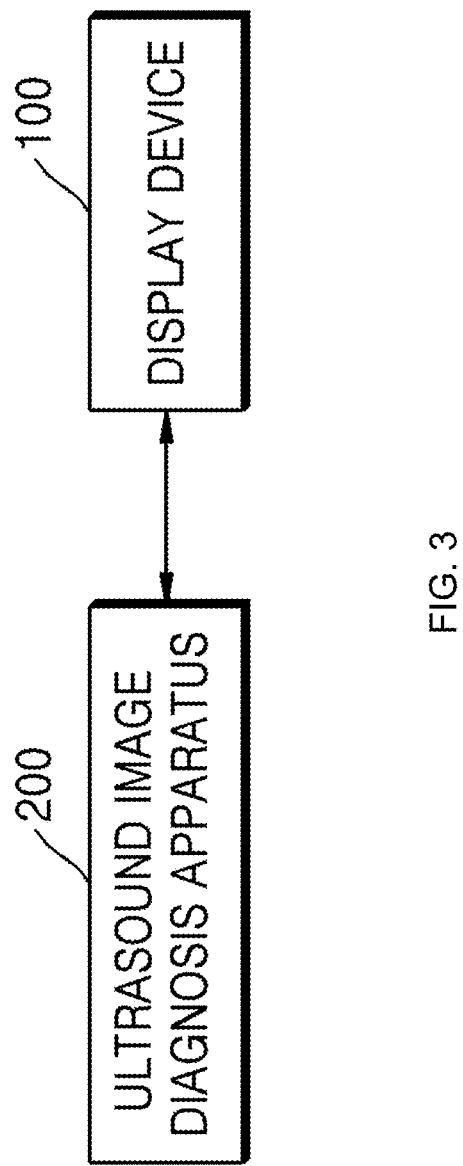
FIG. 3 is a block diagram illustrating components of an ultrasound image display system according to another embodiment of the present invention.

FIG. 3 is a block diagram illustrating components of an ultrasound image display system according to another embodiment of the present invention.

Referring to FIG. 3, the ultrasound image display system may include the display device 100 and an ultrasound image diagnosis apparatus 200.

The display device 100 receives ultrasound image data from the ultrasound image diagnosis apparatus 200 and displays an ultrasound image corresponding to the received ultrasound image data on a touch screen using the received ultrasound image data. Since the display device 100 has been described above with reference to FIG. 1, a detailed description thereof will be omitted below.

The ultrasound image diagnosis apparatus 200 generates ultrasound image data corresponding to biological tissue using an ultrasound probe and transmits the generated ultrasound image data to the display device 100.

Figure 4:
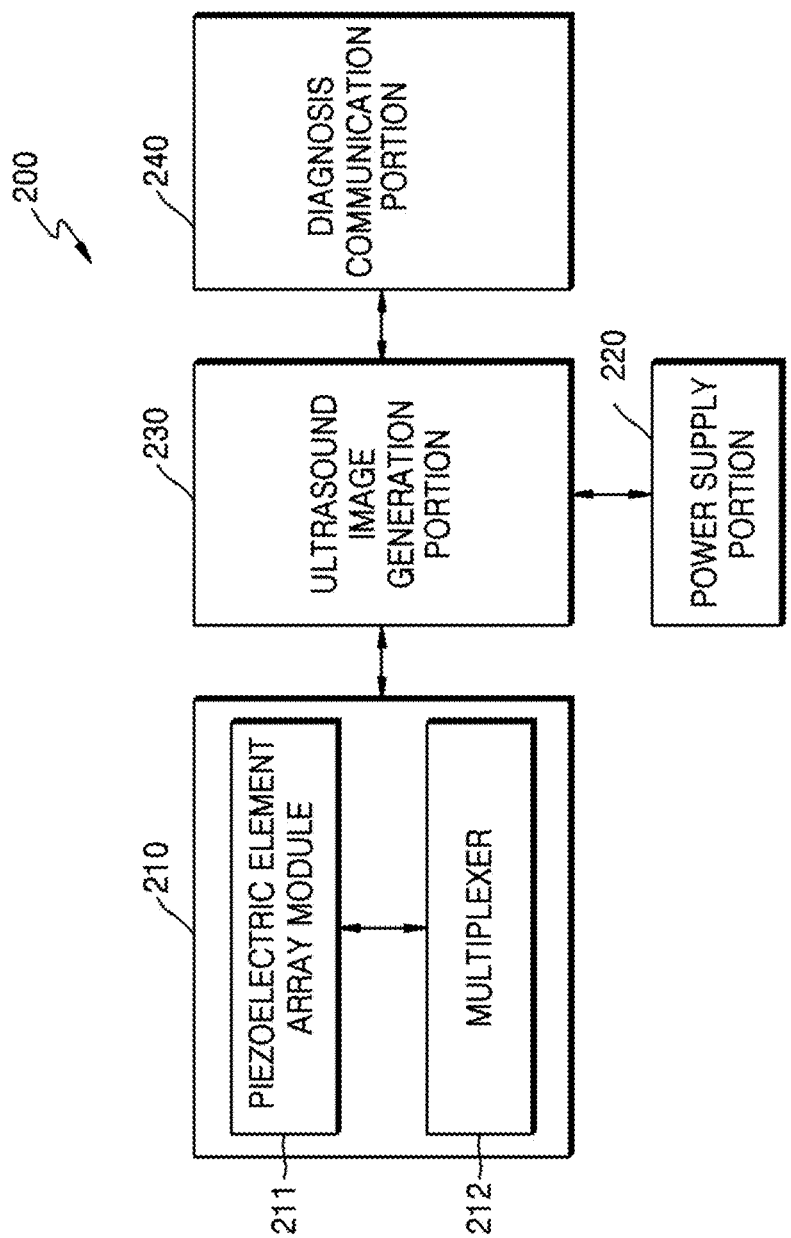
FIG. 4 is a block diagram illustrating components of an ultrasound image diagnosis apparatus shown in FIG. 3 according to one embodiment.

FIG. 4 is a block diagram illustrating components of the ultrasound image diagnosis apparatus 200 shown in FIG. 3 according to one embodiment.

Referring to FIG. 4, the ultrasound image diagnosis apparatus 200 may include an ultrasound probe 210, a power supply portion 220, an ultrasound image generation portion 230, and a diagnosis communication portion 240.

The ultrasound probe 210 transmits an ultrasonic signal to an object to be inspected and receives an ultrasonic echo signal reflected from the object. To this end, the ultrasound probe 210 may include a piezoelectric element array module 211 and a multiplexer 212. Here, the piezoelectric element array module 211 and the multiplexer 212 include piezoelectric elements to generate ultrasonic waves and receive echo signals.

The piezoelectric element array module 211 includes a piezoelectric material. The piezoelectric material oscillates due to an electrical pulse signal and generates and transmits a pulse of an ultrasonic wave to an inside of the object. Also, the piezoelectric material receives an ultrasonic echo signal reflected from the object and converts the ultrasonic echo signal into an electrical signal. Recently, as the piezoelectric material, piezoelectric ceramic such as lead zirconate titanate (PZT) having highest electroacoustic conversion efficiency is generally used. The piezoelectric element array module 211 is generally configured to arrange a large number, such as 64, 128, 192, or the like, of piezoelectric elements in an array form. Here, a range of an electrical pulse which drives the piezoelectric element includes a high voltage from +100 V to −100 V. The piezoelectric element array module 211 may be referred to as an ultrasound transducer.

The multiplexer 212 is configured to reduce the number of signal pins and matches the number of signal lines between the piezoelectric element array module 211 and the ultrasound image generation portion 230. That is, the multiplexer 212 electrically selects and connects elements of the piezoelectric element array module 211 to the ultrasound image generation portion 230 so as not to use all the elements of the piezoelectric element array module 211 at the same time when an ultrasonic signal is transmitted and an ultrasonic echo signal is received but to use only some elements at a position from which the ultrasonic echo signal is collected. For example, the number of piezoelectric elements of the piezoelectric element array module 211 is 64, 128, 192, or the like. Here, the number of signal lines may be significantly reduced using the multiplexer 212.

The power supply portion 220 includes a battery (not shown) charged with power and exhausting the power and supplies power for driving the ultrasound image generation portion 230 using power charged in the battery. The power supply portion 220 includes high voltage for driving the ultrasound probe 210 and supplies power needed in the ultrasound image diagnosis apparatus 200. Here, the power supply portion 220 may perform operations of supplying power and stopping power supply to minimize power consumption caused by operations so as to secure maximum use time while using the battery having limited power as a power source. For example, the power supply portion 220 may include a direct current (DC)-DC converter (not shown). In this case, supplied power may be adjusted through pulse width modulation of the DC-DC converter.

The ultrasound image generation portion 230 generates ultrasound image data of the object. That is, the ultrasound image generation portion 230 may control generation of a high-voltage electrical pulse for generating an ultrasonic signal to be applied to the object, may receive an ultrasonic echo signal provided from the piezoelectric element array module 211 of the ultrasound probe 210, and may generate ultrasound image data by analyzing and processing a difference in intensities of the ultrasonic echo signals. Subsequently, the ultrasound image generation portion 230 controls the generated ultrasound image data to be transmitted to the display device 100.

Figure 5:
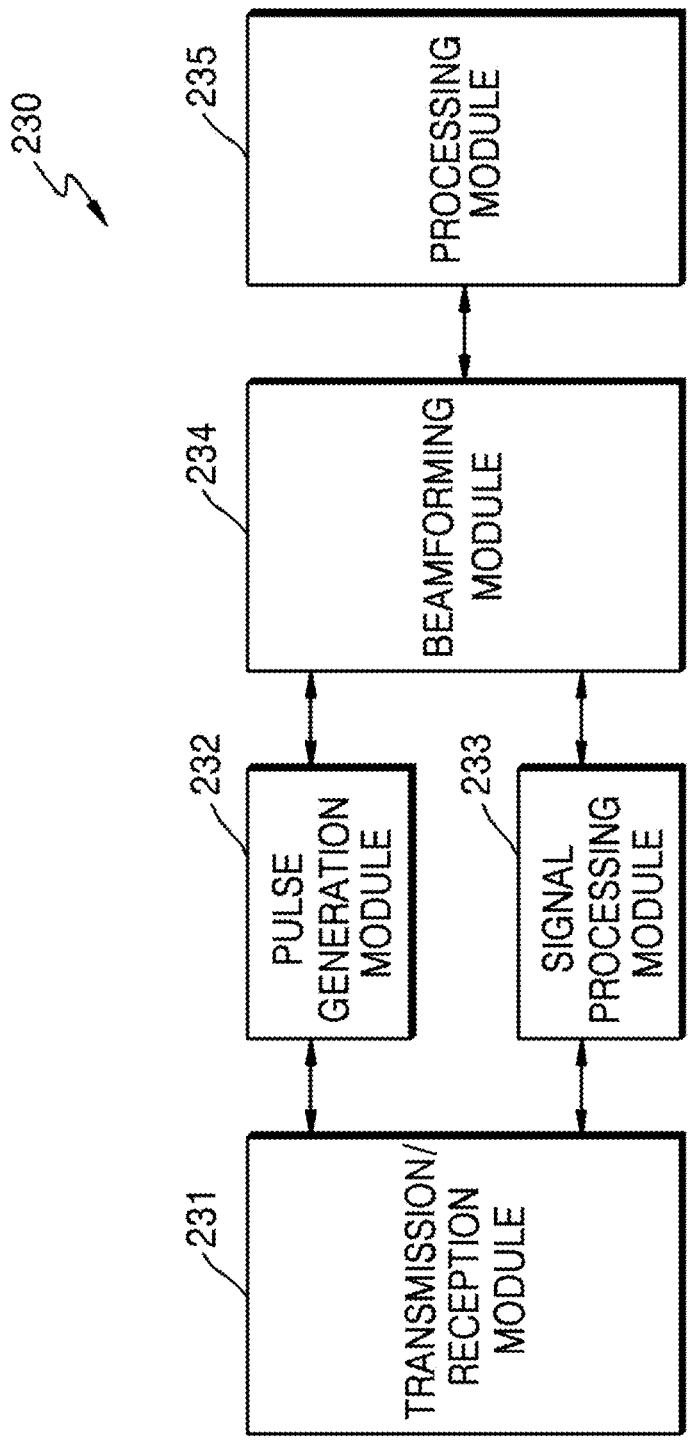
FIG. 5 is a block diagram illustrating components of an ultrasound image generation portion shown in FIG. 4 according to one embodiment.

FIG. 5 is a block diagram illustrating components of the ultrasound image generation portion 230 shown in FIG. 4 according to one embodiment.

Referring to FIG. 5, the ultrasound image generation portion 230 may include a transmission/reception module 231, a pulse generation module 232, a signal processing module 233, a beamforming module 234, and a processing module 235.

The transmission/reception module 231 transmits a high-voltage pulse signal generated by the pulse generation module 232 to the ultrasound probe 210 or transmits an analog signal received from the ultrasound probe 210 to the signal processing module 233 under the control of the processing module 235. That is, when an ultrasonic signal is transmitted to the ultrasound probe 210, the transmission/reception module 231 performs a switching operation of connecting a TX circuit including the pulse generation module 232, the beamforming module 234, and the processing module 235 to the piezoelectric element array module 211 of the ultrasound probe 210. Also, when an ultrasonic echo signal is received, the transmission/reception module 231 performs a switching operation of connecting an RX circuit including the signal processing module 233, the beamforming module 234, and the processing module 235 to the piezoelectric element array module 211.

The pulse generation module 232 generates a high-voltage electrical pulse to be applied to the piezoelectric element array module 211 so as to generate an ultrasonic signal. The pulse generation module 232 generates a high-voltage pulse according to power provided from the power supply portion 220 and transmits the generated high-voltage pulse to the transmission/reception module 231.

The signal processing module 233 converts an ultrasonic echo signal corresponding to an analog signal reflected by the object into a digital signal. Since the ultrasound signal is applied to the object, an energy loss occurs in the ultrasonic echo signal reflected by a spot deep in the object. Particularly, as a reflection depth with respect to the object increases, the energy loss of the ultrasonic echo signal increases. Accordingly, it is necessary to compensate the ultrasonic echo signal. To this end, the signal processing module 233 amplifies the ultrasonic echo signal received through the transmission/reception module 231 and compensates damping of the ultrasonic echo signal according to the reflection depth. The signal processing module 233 may adjust amplification of the ultrasonic echo signal according to the reflection depth or an arrival time of signal. Subsequently, the signal processing module 233 converts the amplified ultrasonic echo signal into a digital signal and transmits the digital signal to the beamforming module 234.

The beamforming module 234 allows the pulse generation module 232 to generate a high-voltage pulse corresponding to the ultrasound probe 210, receives the digital signal from the signal processing module 233, and generates ultrasound image data (hereinafter, referred to as ultrasound scan data) corresponding to the ultrasound probe 210.

TX beamforming includes allowing the pulse generation module 232 to generate the high-voltage pulse adequate for the ultrasound probe 210 using a parameter adequate for the ultrasound probe 210. The beamforming module 234 performs TX beamforming by delaying time in the electrical pulse according to a position of the piezoelectric element so as to focus energy of ultrasonic wave at a focal point at a particular distance when the ultrasonic wave is transmitted Also, RX beamforming includes receiving the digital signal of the ultrasonic echo signal converted by the signal processing module 233, converting data to be adequate for the ultrasound probe 210, and transmitting the converted data to the processing module 235. The beamforming module 234 performs RX beamforming by delaying time of an electrical signal output from each piezoelectric element according to a position and a reception time of the piezoelectric element when the ultrasonic echo signal is received, and generating the ultrasound image data, that is, scan data by adding time-delayed signals.

The processing module 235 controls operations of the whole components included in the ultrasound image diagnosis apparatus 200, that is, the transmission/reception module 231, the pulse generation module 232, the signal processing module 233, and the beamforming module 234.

The processing module 235 controls the beamforming module 234 to perform beamforming adequate for the ultrasound probe 210 and controls the ultrasound image data received from the beamforming module 234 to be transmitted to the display device 100 through the diagnosis communication portion 240. Here, the processing module 235 may compress the ultrasound image data to reduce a bandwidth of a transmission line used for data transmission.

The diagnosis communication portion 240 is configured to transmit and receive data with the display device 100 and may transmit ultrasound image data to the display device 100 under the control of the ultrasound image generation portion 230. The diagnosis communication portion 240 may use a wired communication method or a wireless communication method to transmit the ultrasound image data.

As the wired communication method, the diagnosis communication portion 240 may transmit and receive data using a cable such as a USB cable and the like and may include a module supporting the wired communication method to this end. Also, as the wireless communication method, the diagnosis communication portion 240 may transmit or receive data using one of Bluetooth, wireless USB, wireless local area network (LAN), WiFi, ZigBee, and infrared data association (IrDA) and may include a module supporting the wireless communication method to this end.

Meanwhile, mutually independent structures of the ultrasound image diagnosis apparatus 200 and the display device 100 have been described above. Accordingly, for example, the ultrasound image diagnosis apparatus 200 transmits ultrasound image data to the display device 100 having an independent structure through the diagnosis communication portion 240. However, the ultrasound image diagnosis apparatus 200 and the display device 100 may be an integrated functional block structure for signal transmission. Accordingly, the ultrasound image data generated by the ultrasound image diagnosis apparatus 200 may be sent to the display device 100 corresponding to the integrated functional block for signal transmission to be output.

Figure 6:
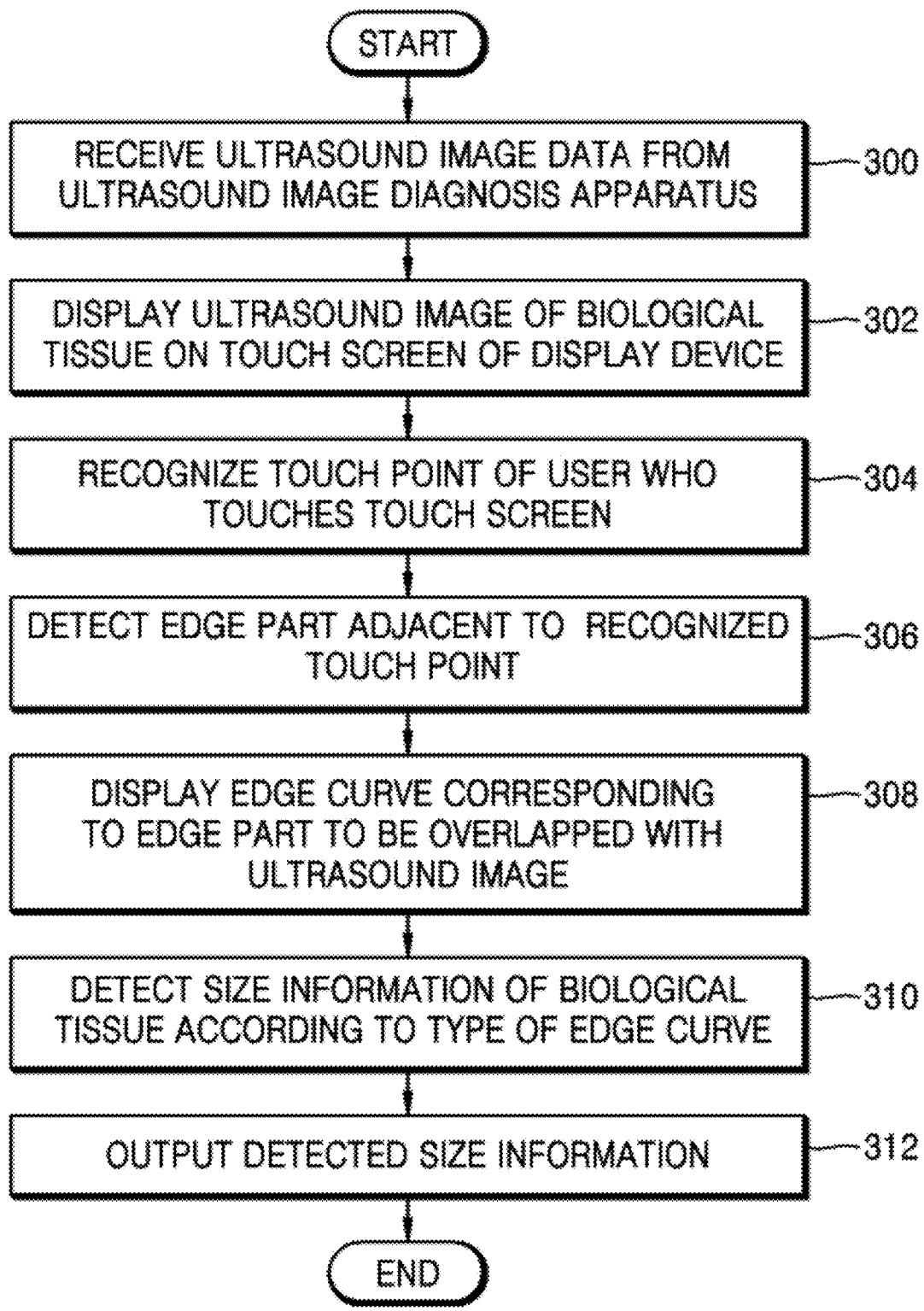
FIG. 6 is a flowchart illustrating one embodiment of a method of detecting a size of biological tissue using the ultrasound image display device according to one embodiment of the present invention.

FIG. 6 is a flowchart illustrating one embodiment of a method of detecting a size of biological tissue using the ultrasound image display device according to one embodiment of the present invention.

First, the display device receives ultrasound image data from the ultrasound image diagnosis apparatus which generates ultrasound image data corresponding to biological tissue (300). However, when ultrasound image data is pre-stored in the display device, the operation of receiving the ultrasound image data from the ultrasound image diagnosis apparatus may be omitted.

After operation 300, the display device displays the ultrasound image of the biological tissue on a touch screen (302).

After operation 302, the display device recognizes a touch point of a user which touches the touch screen on which the ultrasound image is displayed (304). The display device may recognize the touch point of the user by checking a coordinate value of the touch point on the touch screen where the user touches. For example, when the user touches a central part of a blood vessel in the ultrasound image on the touch screen with a finger, the display device recognizes a corresponding touch point as a touch point of the user.

After operation 304, the display device detects one or more edge parts adjacent to the recognized touch point in the ultrasound image (306). The display device may detect an edge part most adjacent to the touch point using an image processing algorithm for detecting an edge.

For example, the display device may detect, as edge parts, points which have a brightness variation higher than or equal to a threshold on the basis of the touch point from a grayscale image of the ultrasound image. To detect the edge part, the display device determines whether a brightness value of the adjacent point is higher than or equal to a certain threshold in comparison to a brightness value of the touch point. When the brightness value of the adjacent point is lower than the certain threshold in comparison to the brightness value of the touch point, the display device determines that a corresponding image region is not the edge part. Also, when the brightness value of the adjacent point is higher than or equal to the certain threshold in comparison to the brightness value of the touch point, the display device determines that the corresponding image region is the edge part.

After operation 306, the display device displays an edge curve corresponding to the detected edge part to be overlapped with the ultrasound image (308). The display device displays such edge curves on the ultrasound image to be overlapped with edge parts adjacent to the touch point (for example, a blood vessel wall image or a fetal head image). Here, the display device may display the edge curves as solid lines, dotted lines, or the like and may display the edge curves in color different from color of the edge parts.

After operation 308, the display device detects size information of the biological tissue according to the type of the displayed edge curve (310).

The display device determines whether the type of the edge curve is an open curve or a closed curve and detects size information corresponding to the determined type of curve. The display device may detect whether both ends of the edge curve are connected to each other and determine a curve type of the corresponding edge curve. However, even when both ends of the edge curve are not connected completely, the display device may determine the edge curve to be a closed curve when the curve has a closed curve shape.

When the type of the edge curve is an open curve, the display device may virtually extend normal lines perpendicular to two edge curves formed on both sides of the touch point and may detect a distance between virtual touch points which meet the open edge curves as the size information. Also, when the type of the edge curve is the closed curve, the display device may detect two virtual points corresponding to a longest distance on an edge curve around the touch point and may detect, as size information, a first distance of a virtual line connecting the detected virtual points and a second distance between two virtual touch points corresponding to a longest distance among virtual touch points at which a virtual normal line perpendicular to the virtual line meets the edge curve or may detect an approximate perimetric length, that is, size information of the closed edge curve using a formula for obtaining a perimetric length with respect to an elliptical closed curve, a circular closed curve, or the like on the basis of the first distance and the second distance.

After operation 310, the display device outputs the detected size information (312). The display device may display the size information of the biological tissue in the ultrasound image on the touch screen or may output the size information as voice information.

The embodiments of the present invention have been described above with reference to the drawings. However, the above description intends only to describe the present invention and not to limit or restrict the content of the present invention. Therefore, a variety of modifications and other equivalent embodiments of the present invention may be implemented by one of ordinary skill in the art. Accordingly, the technical scope of the present invention should be determined by the technical concept of the following claims.

What is claimed is:

1. An ultrasound image display device comprising:
   an input/output interface portion comprising a touch screen configured to display an ultrasound image of biological tissue, and to recognize a touch point of a user who touches the touch screen on which the ultrasound image is displayed;
   an edge detection portion configured to detect at least one edge part adjacent to the recognized touch point in the ultrasound image; and
   a control portion configured to control an edge curve corresponding to the detected edge part to be displayed on the touch screen while being overlapped with the ultrasound image and to detect size information of the biological tissue according to a type of the displayed edge curve,
   wherein the input/output interface portion is configured to output the detected size information under the control of the control portion,
   wherein the control portion is configured to determine whether the type of the edge curve is an open curve or a closed curve, and
   wherein when the type of the edge curve is the open curve, the control portion is configured to detect, as the size information, a distance between virtual touch points at which extended virtual normal lines perpendicular to two open edge curves formed on both sides of the touch point meet the open edge curves.

2. The ultrasound image display device of claim 1, wherein the edge detection portion is configured to detect, as the edge part, points having a brightness variation higher than or equal to a threshold on the basis of the touch point from a grayscale image of the ultrasound image.

3. The ultrasound image display device of claim 1, wherein when the type of the edge curve is the closed curve, the control portion is configured to detect two virtual points corresponding to a longest distance on the closed edge curve formed around the touch point and detect size information corresponding to a perimetric length of the closed edge curve using a first distance of a virtual line connecting the detected virtual points and a second distance between two virtual touch points corresponding to a longest distance among virtual touch points at which a virtual normal line perpendicular to the virtual line meets the closed edge curve.

4. The ultrasound image display device of claim 1, further comprising a display communication portion configured to receive ultrasound image data from an ultrasound image diagnosis apparatus configured to generate the ultrasound image data corresponding to the biological tissue using an ultrasound probe,
   wherein when the ultrasound image data is received through the display communication portion, the input/output interface portion configured to display an ultrasound image corresponding to the received ultrasound image data on the touch screen.

5. An ultrasound image display system comprising:
   an ultrasound image diagnosis apparatus configured to generate ultrasound image data corresponding to biological tissue using an ultrasound probe and to transmit the generated ultrasound image data; and
   a display device configured to receive the ultrasound image data from the ultrasound image diagnosis apparatus and to display an ultrasound image corresponding to the ultrasound image data using the received ultrasound image data,
   wherein the display device comprises:
   an input/output interface portion comprising a touch screen configured to display the ultrasound image, and to recognize a touch point of a user who touches the touch screen on which the ultrasound image is displayed;
   an edge detection portion configured to detect at least one edge part adjacent to the recognized touch point in the ultrasound image; and
   a control portion configured to control an edge curve corresponding to the detected edge part to be displayed on the touch screen while being overlapped with the ultrasound image and to detect size information of the biological tissue according to a type of the displayed edge curve, and
   wherein the input/output interface portion is configured to output the detected size information under the control of the control portion, wherein the control portion is configured to determine whether the type of the edge curve is an open curve or a closed curve, and wherein when the type of the edge curve is the open curve, the control portion is configured to detect, as the size information, a distance between virtual touch points at which extended virtual normal lines perpendicular to two open edge curves formed on both sides of the touch point meet the open edge curves.

6. The ultrasound image display system of claim 5, wherein the ultrasound image diagnosis apparatus comprises:

the ultrasound probe configured to transmit an ultrasonic signal to the biological tissue and then to receive an ultrasonic echo signal reflected from the biological tissue;

an ultrasound image generation portion configured to generate ultrasound image data corresponding to the ultrasonic echo signal received by the ultrasound probe;

a diagnosis communication portion configured to transmit the generated ultrasound image data to the display device; and a power supply portion comprising a battery charged with power and exhausting the power and configured to supply power for driving the ultrasound image generation portion and the communication portion using the power charged in the battery.

7. The ultrasound image display system of claim 6, wherein the ultrasound image generation portion comprises:

a pulse generator configured to generate a high-voltage electrical pulse for generating the ultrasonic signal;

a signal processor configured to amplify and convert the ultrasonic echo signal into a digital signal;

a transmitter/receiver configured to transmit the high-voltage pulse generated by the pulse generator to the ultrasound probe or to receive and forward the ultrasonic echo signal from the ultrasound probe to the signal processor;

a beamformer configured to allow the pulse generator to generate the high-voltage pulse corresponding to the ultrasound probe, to receive the digital signal from the signal processor, and to generate the ultrasound image data corresponding to the ultrasound probe; and a processor configured to control the beamformer to perform beamforming corresponding to the ultrasound probe and to control the ultrasound image data received from the beamformer to be transmitted to the display device.

8. The ultrasound image display system of claim 5, wherein when the type of the edge curve is the closed curve, the control portion is configured to detect two virtual points corresponding to a longest distance on the closed edge curve formed around the touch point and detect size information corresponding to a perimetric length of the closed edge curve using a first distance of a virtual line connecting the detected virtual points and a second distance between two virtual touch points corresponding to a longest distance among virtual touch points at which a virtual normal line perpendicular to the virtual line intersects with the closed edge curve.

9. A method of detecting a size of biological tissue using an ultrasound image display device, the method comprising:

displaying an ultrasound image of biological tissue on a touch screen;

recognizing a touch point of a user who touches the touch screen on which the ultrasound image is displayed;

detecting at least one edge part adjacent to the recognized touch point from the ultrasound image;

displaying, on the touch screen, an edge curve corresponding to the detected edge part to be overlapped with the ultrasound image; and detecting size information of the biological tissue according to a type of the displayed edge curve; and outputting the detected size information, wherein the detecting of the size information of the biological tissue includes determining whether the type of the edge curve is an open curve or a closed curve, and detecting, when the type of the edge curve is the open curve, as the size information, a distance between virtual touch points at which extended virtual normal lines perpendicular to two open edge curves formed on both sides of the touch point meet the open edge curves.

10. The method of claim 9, wherein the detecting of the edge part comprises detecting, as the edge part, points having a brightness variation higher than or equal to a threshold on the basis of the touch point from a grayscale image of the ultrasound image.

11. The method of claim 9, wherein the detecting of the size information of the biological tissue comprises, when the type of the edge curve is the closed curve, detecting two virtual points corresponding to a longest distance on the closed edge curve formed around the touch point and detecting size information corresponding to a perimetric length of the closed edge curve using a first distance of a virtual line connecting the detected virtual points and a second distance between two virtual touch points corresponding to a longest distance among virtual touch points at which a virtual normal line perpendicular to the virtual line meets the closed edge curve.

12. The method of claim 9, further comprising receiving ultrasound image data from an ultrasound image diagnosis apparatus configured to generate the ultrasound image data corresponding to the biological tissue using an ultrasound probe, wherein the ultrasound image is displayed on the touch screen after the receiving of the ultrasound image data.

\* \* \* \* \*